(12) United States Patent
Schreinemakers

(10) Patent No.: US 6,247,925 B1
(45) Date of Patent: Jun. 19, 2001

(54) DENTAL-IMPRESSION TRAY

(76) Inventor: Josephus Schreinemakers, Oranje Nassaulaan 12, 6026 Maarheeze (NL)

(*) Notice: Subject to any disclaimer, the term of this patent is extended or adjusted under 35 U.S.C. 154(b) by 0 days.

(21) Appl. No.: 09/578,606

(22) Filed: May 25, 2000

(30) Foreign Application Priority Data

Nov. 12, 1997 (DE) ................................................. 19750092

(51) Int. Cl.⁷ .................................................... A61C 9/00
(52) U.S. Cl. ................................................. 433/37; 433/47
(58) Field of Search ........................................ 433/37–48

(56) References Cited

U.S. PATENT DOCUMENTS

| | | | |
|---|---|---|---|
| 2,352,545 | * 6/1944 | Jefferies | 433/47 X |
| 2,611,959 | * 9/1952 | Baum | 433/47 |
| 4,146,963 | * 4/1979 | Schreinmakers | 433/37 |
| 4,368,040 | 1/1983 | Weissman . | |
| 4,375,965 | * 3/1983 | Weissman | 433/37 |
| 5,551,872 | * 9/1996 | Mena | 433/37 |
| 5,890,894 | * 4/1999 | Mio et al. | 433/37 |
| 5,890,895 | * 4/1999 | Tucker | 433/37 |

FOREIGN PATENT DOCUMENTS 33 44 774   6/1985 (DE) .
38 37 585   5/1990 (DE) .

* cited by examiner

*Primary Examiner*—Nicholas D. Lucchesi
(74) *Attorney, Agent, or Firm*—Herbert Dubno; Andrew Wilford

(57) ABSTRACT

A tray for taking a dental impression from a jaw having mobile and immobile gum tissues separated at an action line. The tray is formed of a body formed with a U-shaped outer wall having an edge formed as a thickened bead, a U-shaped inner wall spaced inwardly from the outer wall and defining therewith a U-shaped cavity adapted to fit over the jaw with the edge projecting past the action line, a plurality of throughgoing slots on the outer wall immediately adjacent the outer-wall edge and extending generally parallel to the outer-wall edge.

4 Claims, 6 Drawing Sheets

DENTAL-IMPRESSION TRAY

FIELD OF THE INVENTION

The present invention relates to a tray for taking dental impressions. More particularly this invention concerns such a tray used for making impressions used for the manufacture of false teeth.

BACKGROUND OF THE INVENTION

As described in German patent document 3,344,774, a standard tray for taking a dental impression from a jaw having mobile and immobile gum tissues separated at an action line has a body formed with a U-shaped outer or buccal wall having an edge and a U-shaped inner or lingual wall spaced inwardly from the outer wall and defining therewith a U-shaped cavity adapted to fit over the jaw. The U-shaped cavity is dimensioned to fit with some play over the jaw.

In use the cavity is partially filled with impression material and then is forcibly pressed down on the jaw whose impression is to be taken. The impression material is quite viscous so that, when forced against the gum tissues, it push back the mobile tissues and, as a result, the impression will in effect be of the hard tissues of the jaw. The fit is as close as possible so that the impression material is, in effect, pressurized and forced into intimate contact with the immobile tissues of the jaw.

A common problem with such trays is that the impression material pulls out of them. Thus when the material has hardened sufficiently and the tray is lifted, instead of stripping off the patient, the material pulls out of the tray. Then the impression must be peeled off the patient, a procedure that normally damages it and requires that it be taken again.

One solution to this problem has been the use of special bonding agents in the tray that cause the impression material to stick to the tray. While such a system is in theory quite effective, in reality it has numerous drawbacks. The bonding agent must be applied carefully, and must be made of some safe material as it is being put in the patient's mouth. Furthermore if the finished impression is too solidly bonded to the tray, it is itself damaged on removal.

Accordingly U.S. Pat. No. 4,368,040 of Weissmann proposes a tray with numerous cutouts and ridges that cause the impression to interlock with the tray. This purely mechanical coupling is in part effected by causing the impression material to flow out through the tray. As a result the pressure applied to the material to force it against the tissues of the jaw is substantially reduced and the impression is inaccurate.

German published patent application 3,837,585 describes another system where thin slots are cut through the walls of the tray adjacent their edges. Such a system allows the impression mass to be pressurized and does indeed couple the impression to the tray. Nonetheless the material can still pull rather easily out of the tray. In addition the tray itself does not always form a particularly good fit and seal with the jaw.

OBJECTS OF THE INVENTION

It is therefore an object of the present invention to provide an improved dental-impression tray.

Another object is the provision of such an improved dental-impression tray which overcomes the above-given disadvantages, that is which produces a highly accurate impression and which securely holds the thus produced impression so that, when separated from the patient, it stays with the tray.

SUMMARY OF THE INVENTION

A tray for taking a dental impression from a jaw having mobile and immobile gum tissues separated at an action line. The tray is formed of a body formed with a U-shaped outer wall having an edge formed as a thickened bead, a U-shaped inner wall spaced inwardly from the outer wall and defining therewith a U-shaped cavity adapted to fit over the jaw with the edge projecting past the action line, a plurality of throughgoing slots on the outer wall immediately adjacent the outer-wall edge and extending generally parallel to the outer-wall edge.

With this system the only place for the material to escape from the tray is at or adjacent the edge. Thus the material will be highly pressurized in the critical center region, but when the tray is pulled off the jaw the impression will be sure to come with it. The combination of a thickened edge bead and slots immediately adjacent it thus not only improves the quality of the impression, but makes it hold better in the tray.

According to the invention the tray is intended for a lower mandible and its inner wall has an edge and is also formed with a plurality of throughgoing slots immediately adjacent the inner-wall edge and extending generally parallel to the inner-wall edge. The inner-wall edge is also formed as a thickened bead. Thus there is a controlled fit and controlled leakage at the inner edge too.

The slots in accordance with the invention are elongated parallel to the outer-wall edge. They have a length of 0.5 cm to 2 cm, preferably 0.8 cm to 1.7 cm and most preferably of 1.2 cm to 1.6 cm. They have a width of between 1 mm and 3 mm, preferably bout 2 mm. There are two to six, preferably, four such slots on the outer edge and two on the inner edge. The thickened edge has a thickness of from 2 mm to 5 mm, preferably 3 mm.

In use there will therefore be a form of leakage through the slots and, normally, at the small gap between the edge and the jaw tissue. These two leakage flows will typically unite and harden outside the tray so that, when the tray is extracted, it will have a solid bead of impression material around its edge, solidly securing the impression in place. Since the slots are in the action region of the gums the impression will be very accurate once the patient, whose impression is being taken, moves these mobile tissues as is normally done, for instance by extending the tongue when the lower-jaw impression is being taken.

Such a tray can be used with a dentate human jaw. When there are not teeth, a shallower cavity is needed, but even so the system of this invention is highly effective in that it builds up pressure at the critical regions to form an accurate negative impression of these regions.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
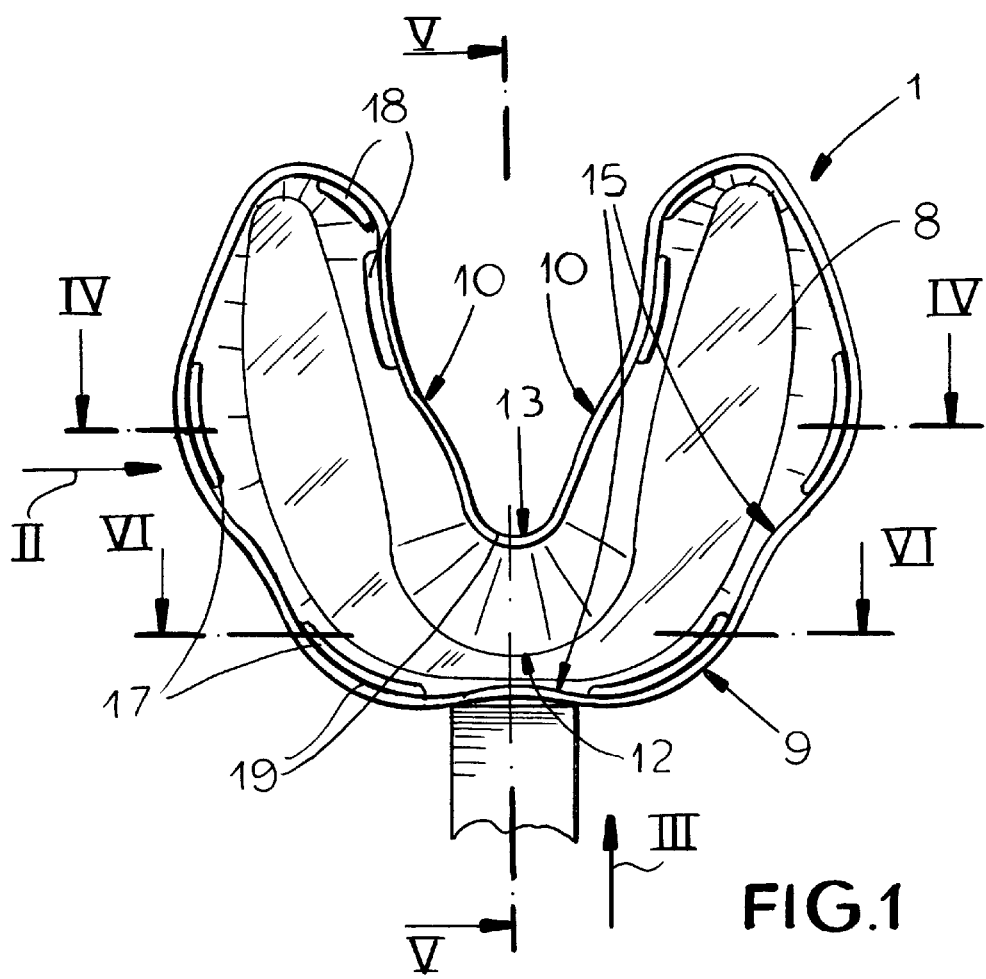
FIG. 1 is a bottom view of a lower-jaw tray according to the invention.
Figure 2:
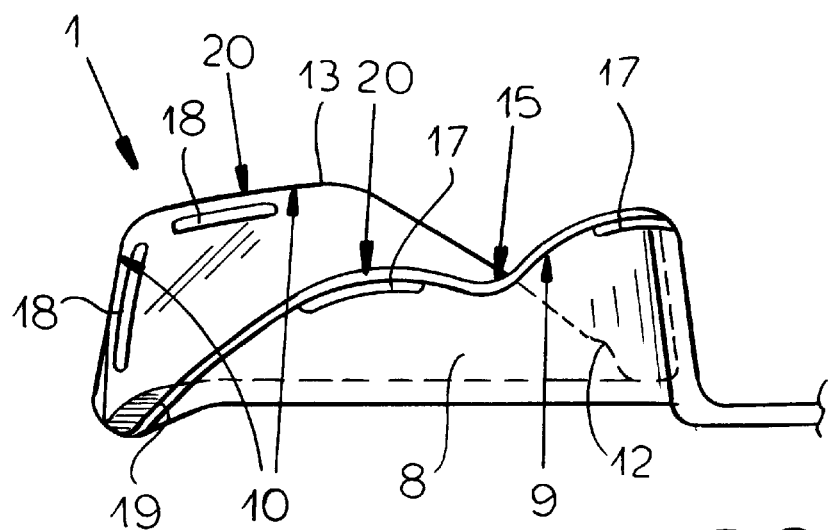
FIGS. 2 and 3 are side and end views taken in the direction of respective arrows II and III of FIG. 1.
Figure 3:
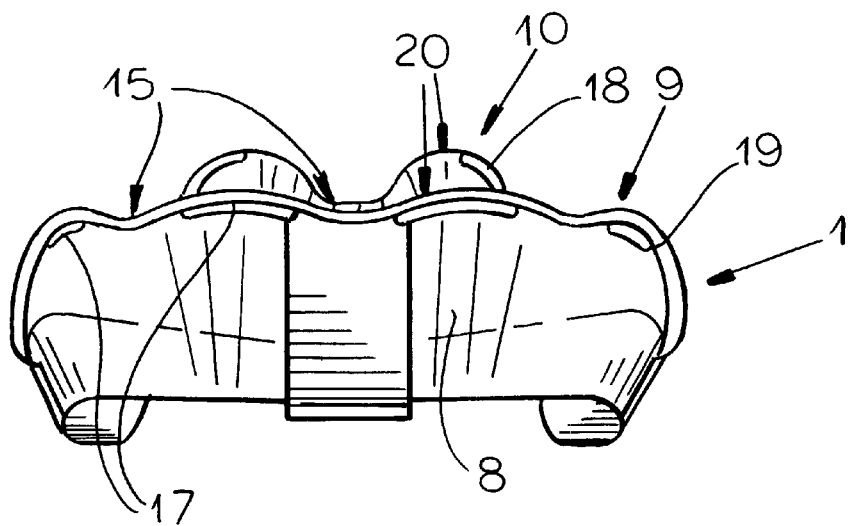

As seen in FIGS. 1 through 6, a lower-jaw dental-impression tray 1 according to the invention is intended for use on a human jaw 3 having teeth 4 projecting from mobile or soft gum tissue 5 and immobile or hard gum tissue 6 joined together at a so-called action line 7. The tray 1 has a U-shaped plastic or metallic body 8 having a U-shaped outer or buccal wall 9 and a U-shaped inner or lingual wall 10 having outer edges 20 formed with a thickened bead 19. Immediately adjacent the bead 19 of the outer wall 9 and parallel thereto are throughgoing slots 17 and similar slots 18 are formed immediately adjacent the bead 19 of the inner wall 10. Otherwise the body 8 is imperforate. The slots are spaced between 1 mm and 3 mm, preferably between 1.5 mm and 2.5 mm, from an outer edge 20 of the bead 19. The edge bead 19 is formed with indents 15 to conform accurately to the patient's mouth. The tray 1 further has to each side of its deepest region 12 a raised region 13 conforming to the shape of the mouth.

Figure 4:
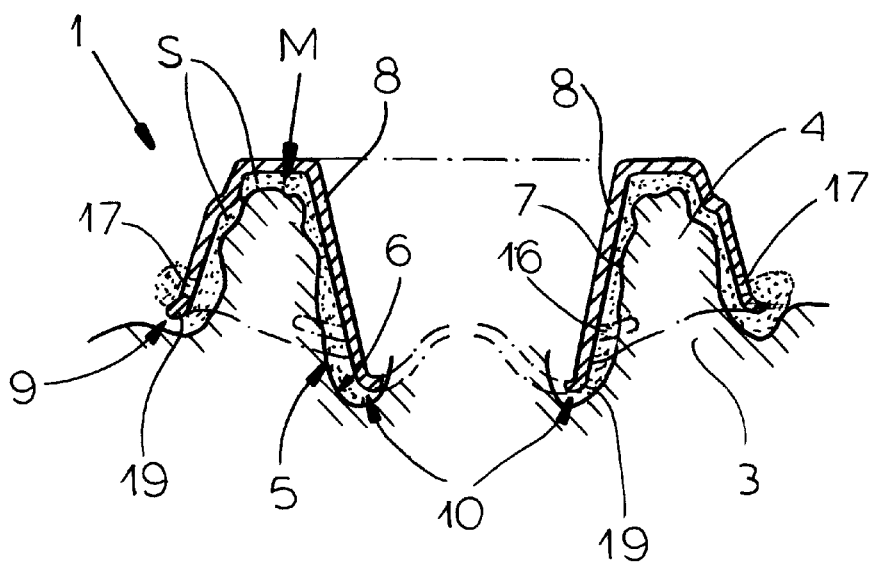
FIGS. 4, 5, and 6 are sections taken along respective lines IV—IV, V—V, and VI—VI of FIG. 1.
Figure 5:
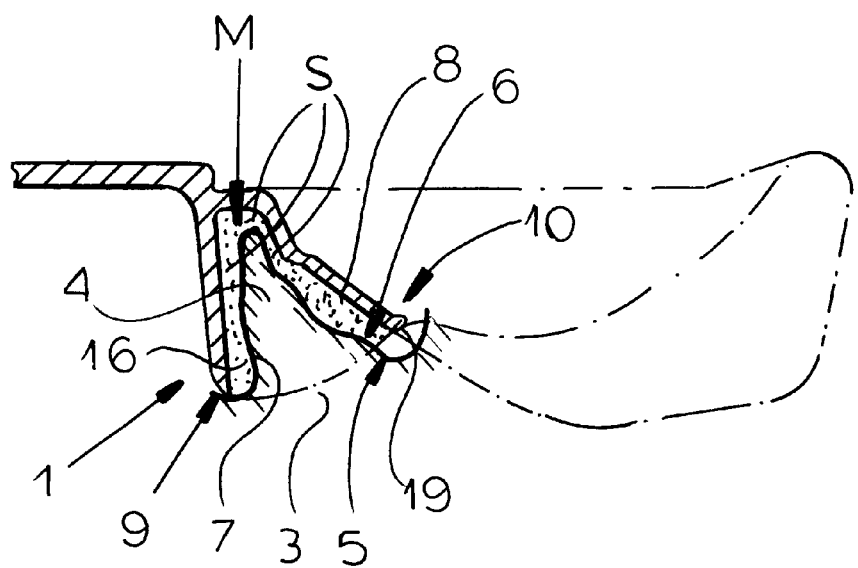
Figure 6:
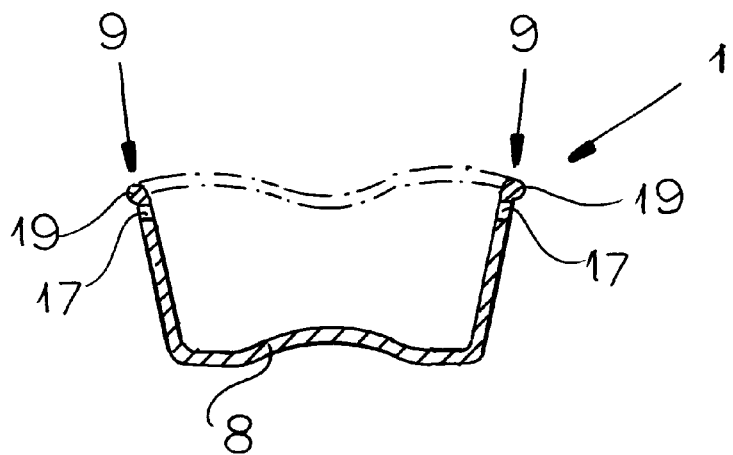
Figure 7:
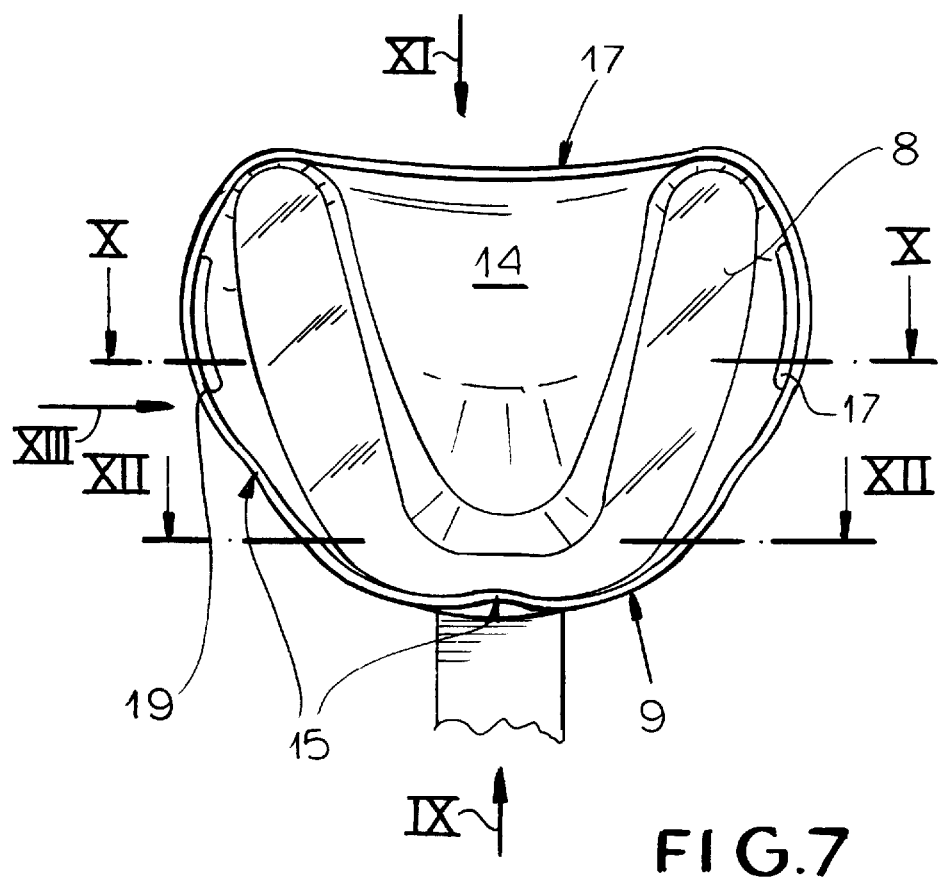
FIG. 7 is a top view of an upper-jaw tray according to the invention.
Figure 8:
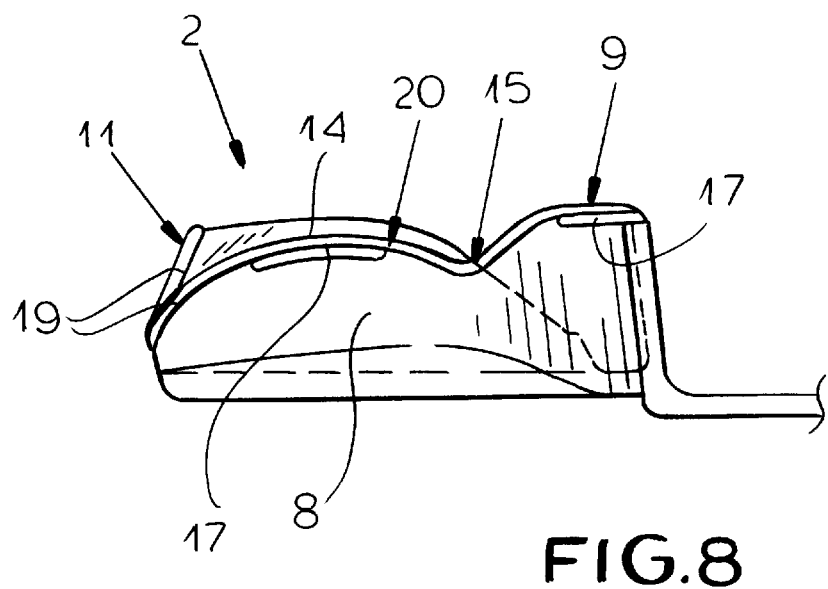
FIGS. 8 and 9 are side and end views taken in the direction of respective arrows VIII and IX of FIG. 7.
Figure 9:
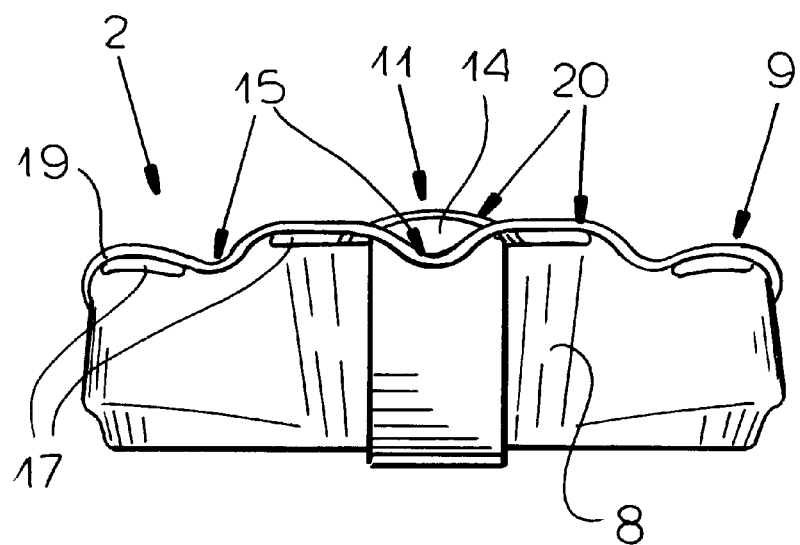
Figure 10:
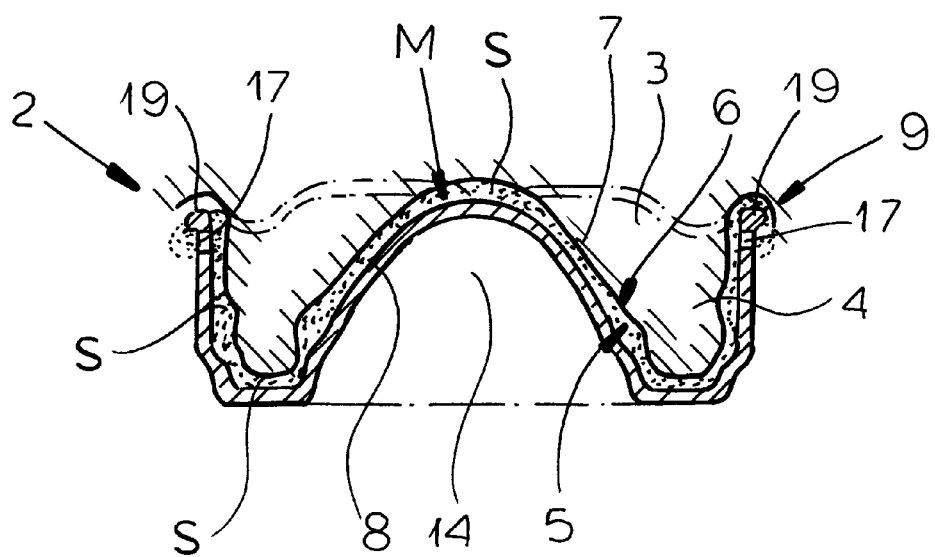
FIG. 10 is a section taken along line X—X of FIG. 7.
Figure 11:
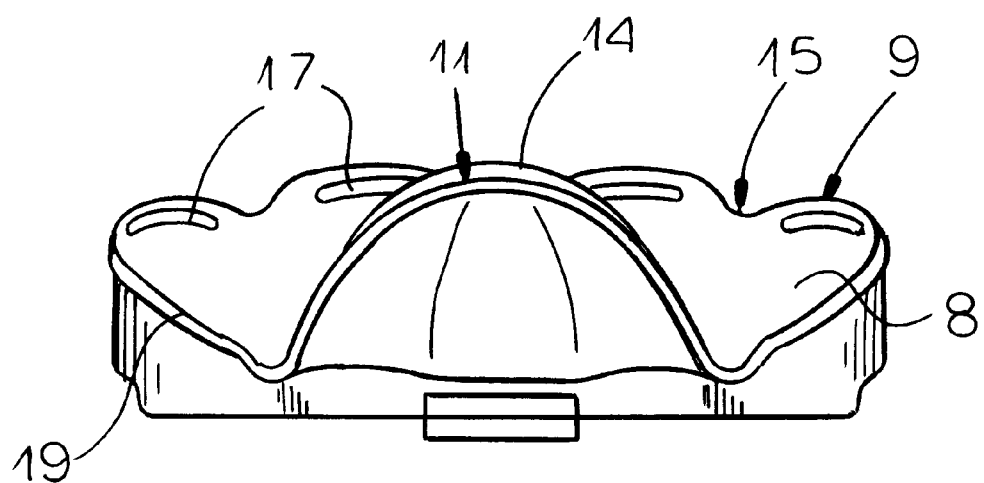
FIG. 11 is an end view taken in the direction of arrow XI of FIG. 7.
Figure 12:
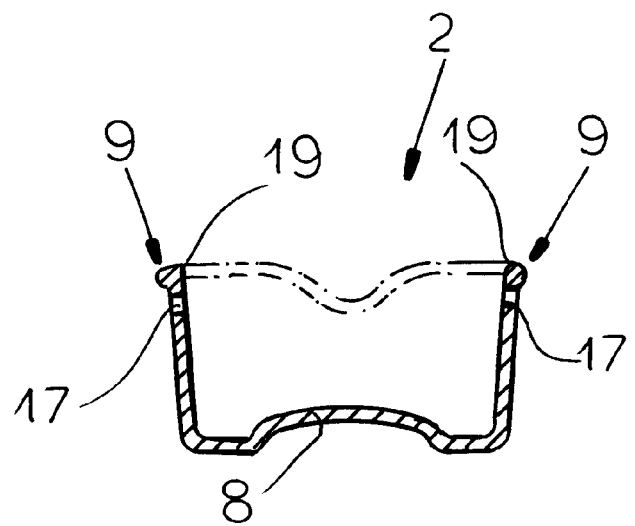
FIG. 12 is a section taken along line XII—XII of FIG. 7.

In use a mass M of impression material is filled into a cavity or chamber 16 formed by the body 8 and same is pressed down over the jaw 3 to form an impression S. The edge bead 19 extends down past the action line 7 and presses against the gum tissues 5 and 6 so that the impression S will conform accurately to the shape of the teeth 4, the pressed-down mobile gum tissue 5, and the adjacent immobile gum tissue 6. It will have a thickness of less than 5 mm. The tray 1 is dimensioned so that a gap of at most 1 mm is produced between the edge bead 19 and the gum tissues 5 and 6. Some of the mass M will extrude out through the slots 17 and 18 and past the edge bead 19, with these masses uniting outside the tray 1 as shown in FIG. 4. Thus the impression S will be locked to the tray 1 so that, once the impression S has hardened, the tray 1 and impression S can be pulled off the teeth 4. No bonding agent is needed to secure the impression S in the tray 1. Furthermore the fit of the tray 1 plus the use of narrow slots 17 and 18 ensures that sufficient pressure can be built up in the cavity 16 to ensure that the mass M exactly conforms to the mouth shape.

In FIGS. 7 through 12 the same reference numerals as in FIGS. 1 through 6 are used for functionally identical structure. Here an upper-jaw tray 2 has its inner walls 11 closed at 14 and adapted to sit against the patient's palate. This inner wall 11 is not formed with slots 18. The impression S will thus extend completely across the patient's palate. This tray 2 is used like the tray 1 of FIGS. 1 through 6.

I claim:

1. A tray for taking a dental impression from a lower human jaw having mobile and immobile gum tissues separated at an action line, the tray being formed of a body formed as one piece with a U-shaped outer wall having an edge formed as a thickened bead;

a U-shaped inner wall spaced inwardly from the outer wall and having an edge formed as a thickened bead, the walls defining a U-shaped cavity adapted to fit over the jaw with the edges projecting past the action line;

a plurality of throughgoing slots on the outer wall immediately adjacent the outer-wall edge and extending generally parallel to the outer-wall edge; and a plurality of throughgoing slots on the inner wall immediately adjacent the inner-wall edge and extending generally parallel to the inner-wall edge, the tray being substantially imperforate except at the outer-wall slots and inner-wall slots.

2. The dental-impression tray defined in claim 1 wherein the slots have length of between 0.5 cm and 2 cm and widths of between 1 mm and 3 mm.

3. A tray for taking a dental impression from an upper human jaw having mobile and immobile gum tissues separated at an action line, the tray being formed of a body formed as one piece with a U-shaped outer wall having an edge formed as a thickened bead;

a U-shaped inner wall spaced inwardly from the outer wall and having an edge;

an imperforate web extending between the inner-wall edges, the walls and web defining a U-shaped cavity adapted to fit over the jaw with the edges projecting past the action line; and a plurality of throughgoing slots on the outer wall immediately adjacent the outer-wall edge and extending generally parallel to the outer-wall edge, the tray being substantially imperforate except at the outer-wall slots.

4. The dental-impression tray defined in claim 3 wherein the slots have length of between 0.5 cm and 2 cm and widths of between 1 mm and 3 mm.

* * * * *